United States Patent [19]

Kyburz et al.

[11] 4,055,431
[45] Oct. 25, 1977

[54] N(β-CHLORO-PROPIONYL OR ACRYLOYL)CARBAMYL OR UREIDO PIPERAZINES

[75] Inventors: Rolf Kyburz, Thun, Switzerland; Rainer Kitzing, Ilford, England

[73] Assignee: Ciba-Geigy AG, Basel, Switzerland

[21] Appl. No.: 681,304

[22] Filed: Apr. 29, 1976

Related U.S. Application Data

[62] Division of Ser. No. 543,752, Jan. 24, 1975, Pat. No. 3,977,881.

[30] Foreign Application Priority Data

Jan. 31, 1974 Switzerland .................. 1332/74

[51] Int. Cl.² .................. G03C 1/30; C07C 127/22; C07D 295/12; B65G 57/10
[52] U.S. Cl. .................. 96/111; 260/112 R; 260/117; 260/268 C; 260/268 R; 260/268 PL; 260/553 E; 214/6 DK; 214/8.5 SS; 271/84
[58] Field of Search ......... 260/268 C, 268 R, 268 PC, 260/112 R, 117; 96/111; 214/1 BB, 6 R, 6 G, 6 F, 6 DK, 8.5 SS; 271/84, 85, 189, 218

[56] References Cited

U.S. PATENT DOCUMENTS

| 3,017,041 | 1/1962 | Hawkes et al. | 214/6 G X |
|---|---|---|---|
| 3,405,932 | 10/1968 | Dame | 214/6 DK X |
| 3,516,653 | 6/1970 | Bland | 271/84 X |
| 3,747,920 | 7/1973 | Linkus | 271/85 |
| 3,833,132 | 9/1974 | Alduk | 214/6 G |
| 3,891,204 | 6/1975 | Mager | 271/85 |
| 3,977,881 | 8/1976 | Kyburz | 96/111 |

Primary Examiner—Donald G. Daus
Assistant Examiner—Jose Tovar
Attorney, Agent, or Firm—Burgess, Dinklage & Sprung; Burns, Doane, Swecker & Mathis

[57] ABSTRACT

This invention relates to new compounds of the formula (1):

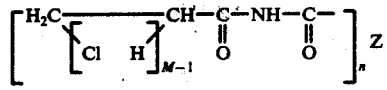

$m$ is 1 or 2, $n$ is 2, 3, 4, 5 or 6, Z represents a polyamine radical containing a basic tertiary or a quaternary nitrogen atom. The compounds of formula ($m$) an useful as crosslinking agents. They are particularly useful for crosslinking gelatine, preferably gelatin present in layers of photographic material.

8 Claims, No Drawings

N(β-CHLORO-PROPIONYL OR ACRYLOYL)CARBAMYL OR UREIDO PIPERAZINES

This is a divisional of application Ser. No. 543,752, filed on Jan. 24, 1975, now U.S. Pat. No. 3,977,811, granted 8/31/76.

The subject of the invention are new acylurea compounds of the formula

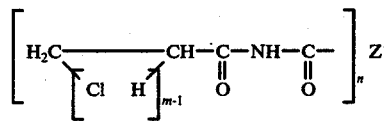

(1)

wherein $m$ is 1 or 2, $n$ denotes an integer of value from 2 to 6 and Z denotes the radical of a polyamine which is bonded by nitrogen atoms to the —CO—NH—CO— groups and in addition to these nitrogen atoms contains at least one tertiary or quaternary nitrogen atom.

If $m$ is 2, the compounds contain β-chloropropionic acid radicals (ClH$_2$C—CH$_2$—CO—). Particularly valuable compounds are in general, those with two acrylic acid radicals (H$_2$C=CH—CO—), that is to say the compounds of the formula (1), wherein $m$ is 1.

The polyamine from which the radical Z is derived possesses $n$ at most secondary (that is to say primary and/or secondary) amino groups, which are then bonded to the acyl groups in the acyl urea compounds of the formula (1):

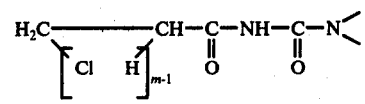

(1a)

The nitrogen atoms can also be members of a preferably saturated heterocyclic ring in which case they participate with two bonds in the ring system. Additionally to the $n$ nitrogen atoms present in the acylamino groups, the remainder of the polyamine must contain at least one tertiary or quaternary nitrogen atom which can also be present in a ring. Such a ring nitrogen atom can also participate with three bonds in the ring system. There are numerous possibilities within this framework. For example, the radical Z can contain two tertiary nitrogen atoms or two quaternary nitrogen atoms or one tertiary or one quaternary nitrogen atom, and the —CO—NH—CO— groups can in part be bonded to nitrogen atoms present in rings and in part to other nitrogen atoms, for example to those in HN> or alkyl-N> groups.

The compounds of the following formulae are preferred:

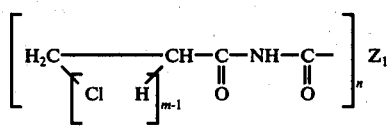

(2)

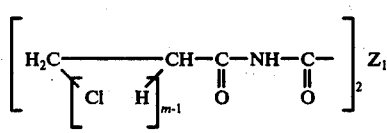

(3)

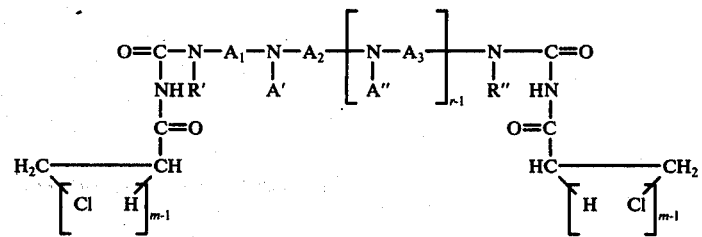

(4)

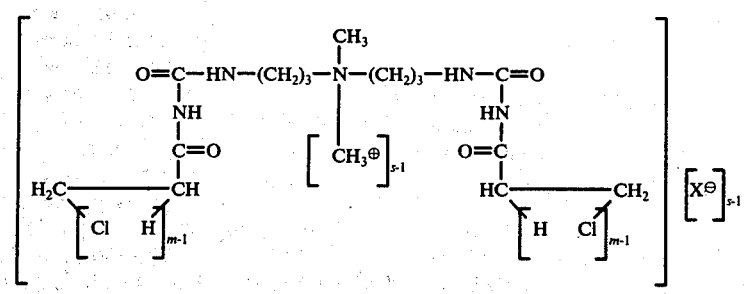

(5)

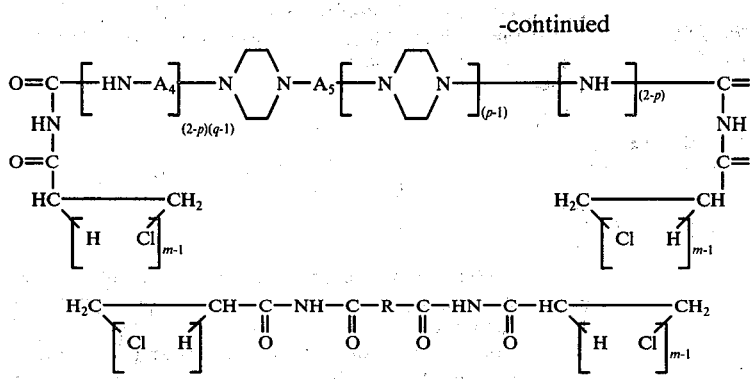

(7)

In the formulae (1) to (7), the individual symbols throughout have the same meaning and in particular denote the following (Z, m and n have already been explained for formula (1)):

p, q, r and s each denote one of the numbers 1 and 2, $Z_1$ denotes the radical of an aliphatic amine, which in addition to aliphatic hydrocarbon radicals can contain saturated heterocyclic rings, and which is bonded by nitrogen atoms to the —CO—NH—CO— group and in addition to these nitrogen atoms contains at least one tertiary or quaternary nitrogen atom, $A_1$, $A_2$, $A_3$, $A_4$ and $A_5$ independently of one another denote alkylene radicals with at most 4 carbon atoms, A' and A" independently of one another denote methyl or ethyl groups, R' and R" independently of one another denote hydrogen atoms or alkyl groups, such as methyl or ethyl groups and R denotes one of the radicals of the formulae

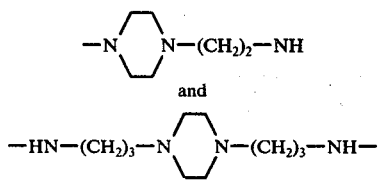

X denotes an anion.

In addition to the tertiary compounds of the formula (3), the corresponding quaternary compounds can also be used, that is to say the compounds in which at least one of the nitrogen atoms bonded to A' and A" is quaternary.

In the case of formula (6) there are three possibilities, depending on the values chosen for p and q, with regard to the radical located between the two —CO— groups:

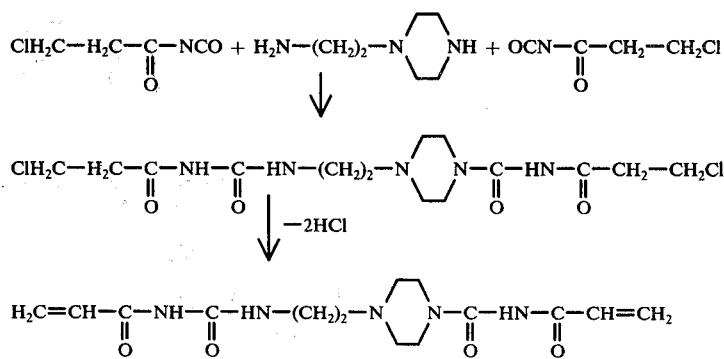

The acylurea compounds of the formulae I to 7 can be obtained by addition of 3-chloropropionyl isocyanate to an amine with n reactive (primary or secondary) amino groups and at least one tertiary amino group or one quaternary ammonium group, in the molecular ratio of n:1. This gives compounds with chloropropionic acid radicals. Such compounds can be converted, by elimination of hydrogen chloride, into the corresponding acrylic acid derivatives. The equations for one such reaction sequence are given below:

$$ClH_2C-H_2C-\underset{\underset{O}{\parallel}}{C}-NCO + H_2N-(CH_2)_2-N\diagdown\diagup NH + OCN-\underset{\underset{O}{\parallel}}{C}-CH_2-CH_2Cl$$

$$\downarrow$$

$$ClH_2C-H_2C-\underset{\underset{O}{\parallel}}{C}-NH-\underset{\underset{O}{\parallel}}{C}-HN-(CH_2)_2-N\diagdown\diagup N-\underset{\underset{O}{\parallel}}{C}-HN-\underset{\underset{O}{\parallel}}{C}-CH_2-CH_2Cl$$

$$\downarrow -2HCl$$

$$H_2C=CH-\underset{\underset{O}{\parallel}}{C}-NH-\underset{\underset{O}{\parallel}}{C}-HN-(CH_2)_2-N\diagdown\diagup N-\underset{\underset{O}{\parallel}}{C}-HN-\underset{\underset{O}{\parallel}}{C}-CH=CH_2$$

The acylurea compounds with tertiary amino groups which are obtainable in this way can also subsequently be converted in a manner which is in itself known into quaternary ammonium compounds. Furthermore, the anions or such quaternary ammonium compounds can be exchanged.

The following are examples of possible anions of quaternary ammonium compounds: halide, nitrate, sulphate, phosphate, carbonate, borate, chlorate, iodate, perchlorate, thiocyanate, methosulphate, ethosulphate, fluorosulphonate, acetate, trifluoroacetate, oxalate, tartrate, benzoate, benzenesulphonate, p-toluenesulphonate, methanesulphonate, tetrafluoroborate, hexafluorophosphate, hexafluoroarsenate, hexafluorotitanate, hexafluoroantimonate, hexafluorostannate, hexachloroantimonate, tetrachloroaurate, tetrachloroaluminate and tetrachloroferrate.

Preferred anions are chloride, iodide, sulphate, methosulphate, perchlorate, hexafluorophosphate, tetrafluoroborate, hexafluoroarsenate and fluorosulphonate.

Examples of suitable starting materials for the manufacture of tertiary and quaternary acylurea compounds of the formula (1) are the following polyamines for which, in the case of the quaternary compounds, only the cation which can be combined with one of the above anions, is shown.

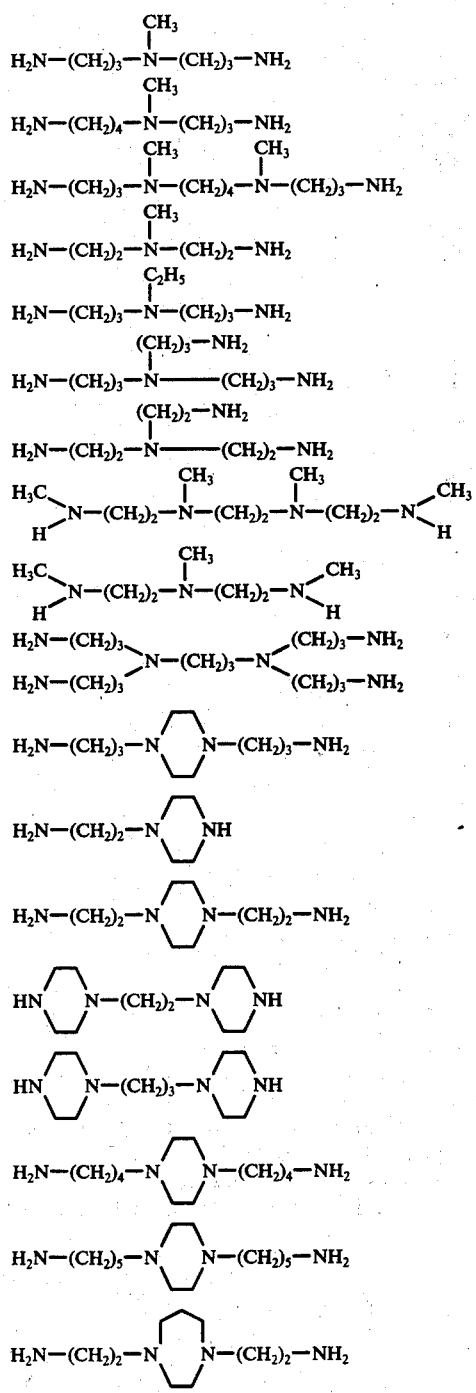

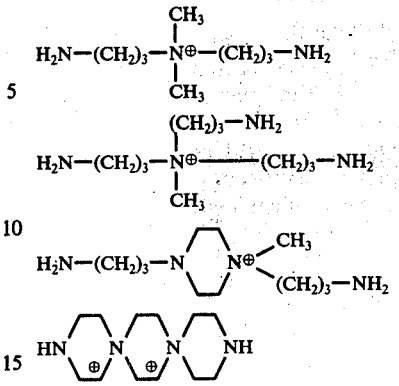

The acylurea compounds of the formula (1) can be used as crosslinking agents in the textile and leather industry, the manufacture of paper and the plastics industry, glue industry and gelatine industry. Above all, they are used as hardeners for water-soluble polymers such as polyvinyl alcohol, gelatine or gelatine derivatives, especially in the form of layers, containing such colloids, of photographic materials. The reaction of these colloids with such compounds in general takes place easily and in the usual manner. As a rule, the compounds are readily water-soluble.

In most cases it suffices to add the products to be used according to the invention, as an aqueous solution or in a solid form which is as finely divided as possible, to an aqueous solution of the hydrophilic colloid, whilst stirring well.

Thus it is possible, for example, to bring a solution of the crosslinking agents in water, but also mixed with, for example, ethanol, methanol or acetone, into contact with the colloids at normal or slightly elevated temperature. Gelatine, which optionally contains silver halide and/or other components required to produce photographic images has proved particularly suitable. The gelatine can be cast on a substrate to form a layer, and be dried, in the usual manner. The layer can then be left for some time, for example up to 24 hours, at an elevated temperature or at room temperature. In the course thereof, hardening occurs rapidly and progressively; the melting point of the gelatine rises substantially, for example by 25° to 60° C, and the reciprocal swelling factor increases correspondingly (compare Table 1).

The amount of hardener used depends on the desired degree of hardening but is suitably 0.1 to 10 per cent by weight, based on the weight of the dry gelatine.

A particular advantage of the present crosslinking agents is that when used in low concentration they impart an adequate degree of hardness to the gelatine layers after only, for example, 24 to 48 hours, so that the cast products can be tested by processing samples immediately following their manufacture, even if the test is carried out at elevated temperature or in (chemically) agressive processing baths.

It is a further advantage that no significant pH change in the emulsion layer occurs during hardening, according to the invention, with the compounds of the formula (1).

The hardened product itself is very stable; even after prolonged storage at temperatures around 40° C and a relative atmospheric humidity of about 70% no decrease in the reciprocal swelling factor is in general observable.

The degree of hardening is also not altered significantly by acids or bases, even on prolonged exposure to these, thereby indicating that the hardener-gelatine bond is very resistant to hydrolysis.

In addition the compounds used according to the invention are, as already mentioned, generally readily soluble in water and very stable in aqueous solutions at low and medium pH values.

The excellent stability and good solubility are both particularly important properties on which, for example, the applicability in photographic techniques depends to a decisive degree. Thus, for example, it is particularly desirable, for the continuous manufacture of photographic materials, that batches of solutions of crosslinking agents should remain stable for several hours or days at room temperature and that the concentration of the hardener, and therefore its ability to crosslink the gelatine, should not decrease, or only do so insignificantly. On the other hand it is equally important that, for the same reason, the hardener should not decompose, or only do so insignificantly, and should not react with water, or only do so insignificantly, in the casting solution at about 40° C during the course of the requisite standing time and residence time, so as to maintain for several hours its full crosslinking action, when casting, drying and storing the photographic material.

Furthermore, the viscosity of the casting solution should not increase significantly during the standing time, as a result of the addition of the hardener. It is also particularly important that the hardener should not cause any yellowing fogging or effect on gradation even on prolonged treatment of the cast layer at elevated temperature and elevated atmospheric humidity.

The compounds of the general formula (1) conform very well to these strict requirements with regard to their stability to hydrolysis.

The hardeners can be used to harden (crosslink) very diverse layers containing gelatine, such as, for example, intermediate layers, emulsion layers, filter layers, base layers, top layers, backing layers and anti-halation layers. The layers can contain not only the crosslinking agents but also additives of the most diverse kind, such as, for example, silver halide, pigments, such as barium sulphate, titanium dioxide or silicon dioxide or organic pigments, such as coloured pigments, as well as image dyestuffs, colour coupling agents, sensitisers, filter dyestuffs, anti-halation dyestuffs and screen dyestuffs, stabilisers, UV absorbers, optical brighteners, crosslinking agents, lubricants, antistatic agents, latices or other crosslinking agents.

In the case of the compounds of relatively low molecular weight it is possible, because of their good diffusibility in a multi-layer material, to add them only to the auxiliary layers in order to achieve, by diffusion, a hardening of the adjacent silver-halide layers. However, with increasing molecular weight, these compounds show decreasing diffusion when used in photographic layers and if the molecular weights are sufficiently high diffusion-resistant crosslinking agents are obtained. This property offers decisive advantages, in several respects, while manufacturing multi-layer materials.

These new crosslinking agents can also be used as mixtures with other compounds suitable for crosslinking water-soluble colloids, especially gelatine.

EXAMPLE 1

143.0 g (1.065 mol) of freshly distilled 3-chloropropionyl isocyanate in 1 l of absolute toluene are first introduced into a 2 l reaction vessel equipped with a stirrer, thermometer and dropping funnel. The mixture is cooled to $-5°$ C and a solution of 72.5 g (0.5 mol) of freshly distilled N,N'-bis-(3-amino-propyl)methylamine in 200 ml of absolute toluene is added dropwise. Hereupon, the reaction product separates out as a white precipitate. After completion of the addition, the mixture is allowed to warm to room temperature and is then left for a further 1½ hours whilst stirring. The product is then filtered off and rinsed with 50 ml of toluene and 50 ml of ether, and dried in a vacuum cabinet at up to 40° C. 208.2 g of the chloropropionyl-urea compound of the formula

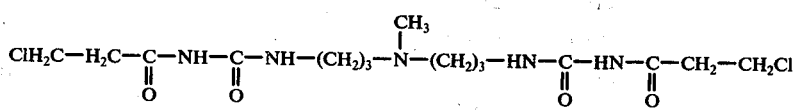

of melting point: 95° C (with decomposition) are obtained in quantitative yield.

EXAMPLE 2

In the same way, reaction of 6.5 g (50 mmols) of N-(2-aminoethyl)piperazine with 14.3 g (106 mmols) of 3-chloropropionyl isocyanate gives a quantitative yield of 19.8 g of the 3-chloropropionyl urea of the formula

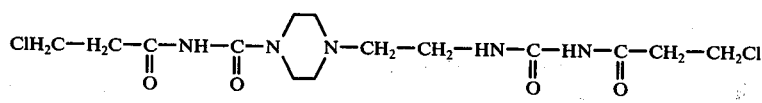

Melting point: 125°–130° C.

EXAMPLE 3

In the same way as in Example 1, reaction of 10.0 g (50 mmols) of N,N'-bis(3-aminopropyl)piperazine with 14.3 g (106 mmols) of 3-chloropropionyl isocyanate gives 24.0 g of the 3-chloropropionylurea compound of the formula

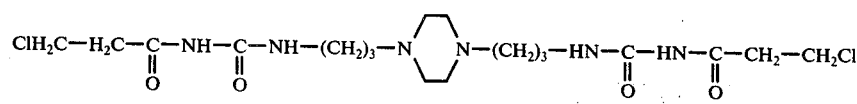

EXAMPLE 4

208.2 g (505 mmols) of the 3-chloropropionylurea obtainable according to Example 1 are dissolved in 1 l of dimethylformamide in a 1.5 l Erlenmeyer flask and 500 mg of hydroquinone are added. A total of 180 ml (1.31 mols) of triethylamine is added gradually whilst stirring constantly; in the course thereof, the temperature should not rise above 30° C. The mixture is stirred for a further 18 hours and the triethylammonium chloride which has precipitated is then filtered off. The solvent is cautiously distilled off, almost to dryness, in vacuo at 35° C and the product is suspended in 1 l of acetone. The mixture is stirred for 1½ hours and again filtered. The filter cake is now suspended in one-half l of water, the mixture is stirred and after one-half hour, the product is filtered off and rinsed with a little water. It is dried in a vacuum cabinet and 16.6 g (57%) of the acryloylurea of the formula $$H_2C=HC-\underset{\underset{O}{\|}}{C}-HN-\underset{\underset{O}{\|}}{C}-NH-(CH_2)_3-\underset{\underset{CH_3}{|}}{\overset{\overset{CH_3}{|}}{N}}-(CH_2)_3-HN-\underset{\underset{O}{\|}}{C}-HN-\underset{\underset{O}{\|}}{C}-CH=CH_2$$

of melting point: 112 to 115° C are obtained.

EXAMPLE 5

In the same manner as in Example 4, the reaction of 7.9 g (20 mmols) of the 3-chloropropionylurea from Example 2 with 7.12 ml (52 mmols) of triethylamine gives the acryloylurea of the formula

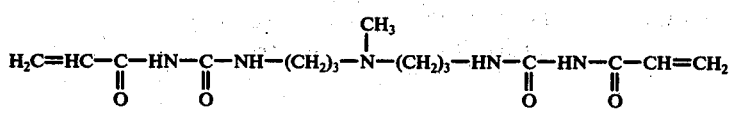

Yield: 4.8 g (75%). Melting point: 155°–157° C (with decomposition).

EXAMPLE 6

In the same manner as in Example 4, the reaction of 9.3 g (20 mmols) of the 3-chloropropionylurea from Example 3 with 7.12 ml (52 mmols) of triethylamine gives the acryloylurea of the formula

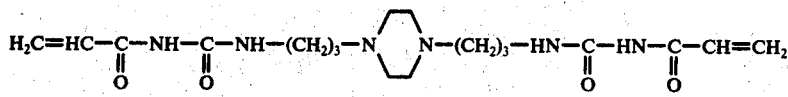

Yield: 4.4 g (62%). Melting point 240° to 245° C (with decomposition).

EXAMPLE 7

6.8 g of N,N'-bis-(3-aminopropyl)-dimethylammonium-p-toluenesulphonate are dissolved in 120 ml of acetonitrile. 5.35 g of β-chloropropionyl-isocyanate in 180 ml of acetonitrile are added dropwise at 0° to 5° C. After stirring, without cooling, for 2 hours, the product is filtered off and washed with acetonitrile. The acetonitrile is distilled off and the residue is dissolved in 40 ml of water, any undissolved residue is filtered off and a precipitate is obtained by adding 8 g of ammonium hexafluorophosphate dissolved in 50 ml of water. The precipitate is filtered off, washed with ice water and alcohol and dried. 8.8 g of the compound of the formula

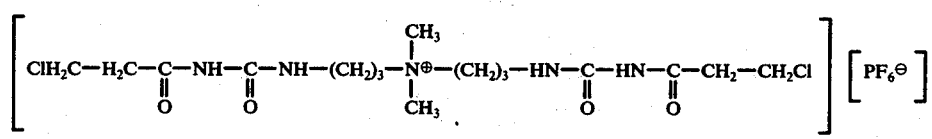

of melting point: 165° C are obtained.

EXAMPLE 8

5.9 g of the product obtained according to Example 7 are dissolved in 200 ml of acetonitrile. 6 g of triethylamine are added. After 24 hours the solvent is distilled off, the residue is taken up in 100 ml of acetone at 40° C and insoluble residues are filtered off. On concentrating the solution, colourless crystals are obtained. These are filtered off, washed with water and dissolved in acetone. 1.4 g of the pure compound of the formula

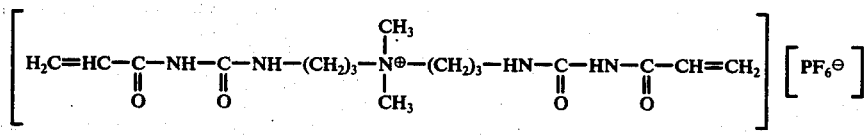

are obtained by precipitation with ether.

EXAMPLE 9

1.9 g of N,N-bis-(3-aminopropyl)-methylamine are dissolved in 125 ml of absolute ether at −10° C. 5.4 g of β-chloropropionyl-isocyanate, dissolved in 25 ml of ether, are added thereto. The precipitate is filtered off and dissolved in 200 ml of acetone, and any undissolved residue is filtered off. After distilling off the solvent, a white powder is left.

Yield: 35 g.

2.5 g of the product thus obtained are shaken with 25 ml of 2 N sodium hydroxide solution. The solution is twice extracted with ethyl acetate and the organic phase is dried with potassium carbonate and mixed with an excess of methyl iodide. The hygroscopic precipitate is dissolved in water and then precipitated from perchlorate. It is then dissolved in acetone and precipitated by adding ether. 0.3 g of the compound of the formula serves to make the samples more readily visible when measuring the swelling.

The samples are stored at room temperature (NS = normal storage, 18° to 22° C, 50% relative atmospheric humidity) or under climatically controlled conditions (CS = climatically controlled storage, 42° to 44° C, 69% relative atmospheric humidity). To determine the reciprocal swelling factor, a thin section, of 20 μ, is produced from each of the samples, and is measured under a microscope. The thickness of the dry gelatine layer is determined, deionized water is then added and after 4 minutes the thickness of the swollen gelatine layer is measured. The reciprocal swelling factor 1/SF

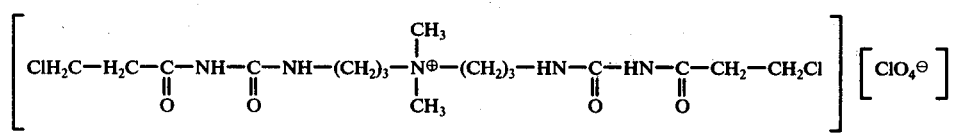

is obtained. Melting point: 163° to 165° C.

EXAMPLE 10

In the text which follows, the reciprocal swelling factor is used as a measure of the hardening. The samples are prepared as follows:

6 ml of a 6% strength gelatine solution, 1 ml of a 1% strength aqueous solution of the dyestuff of the formula corresponds to the following ratio:

$$1/SF = \frac{\text{Thickness of the dry layer}}{\text{Thickness of the swollen layer}}$$

The results are summarised in Table 1; in this table, $R_1$ denotes the radical of the formula $H_2C\!=\!CH\!-\!CO\!-\!NH\!-\!CO\!-$ and $R_2$ denotes the radical of the formula $Cl\!-\!H_2C\!-\!CH_2\!-\!CO\!-\!NH\!-\!CO\!-$.

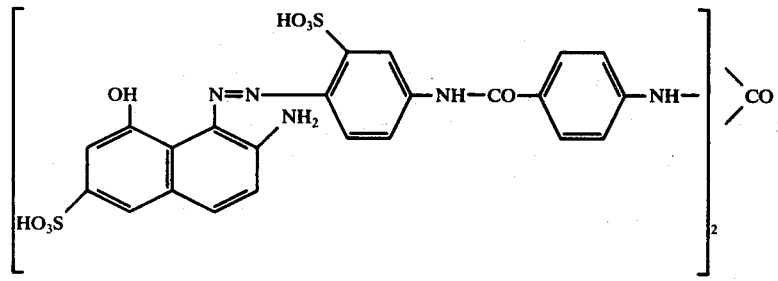

1 ml of an 0.025 molar hardener solution and 5 ml of deionised water are mixed and adjusted to pH = 6.5. The solution is cast on a 13 cm × 18 cm triacetate film. After having solidified at 10° C, the material is dried at 20° C over the course of one hour. The dyestuff merely Particularly in the case of the compounds containing the radical $R_1$, the degree of crosslinking of the gelatine is not impaired on storage under climatically controlled conditions. Even alkaline processing baths are as a rule unable to affect the degree of crosslinking adversely. This applies in particular also to colour developers when processing chromogenic material.

Table 1

| Crosslinking agent of the formula | Prepared according to Example | pH | 1/SF under normal storage after | | | 1/SF under climatically controlled storage after | |
|---|---|---|---|---|---|---|---|
| | | | 3 hours | 2 days | 7 days | 2 days | 7 days |
|  | 5 | 6.5 | 0.069 | 0.153 | 0.198 | 0.338 | 0.347 |
| 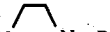 | 4 | 4.5 | 0.075 | 0.100 | 0.131 | 0.354 | 0.345 |
| | | 5.5 | 0.115 | 0.104 | 0.152 | 0.353 | 0.350 |
| | | 6.5 | 0.129 | 0.185 | 0.236 | 0.375 | 0.369 |
| | | 7.5 | 0.179 | 0.219 | 0.250 | 0.372 | 0.354 |
|  | 8 | 4.5 | 0.089 | 0.088 | 0.095 | 0.324 | 0.377 |
| | | 5.5 | 0.077 | 0.100 | 0.139 | 0.370 | 0.375 |
| | | 6.5 | 0.081 | 0.138 | 0.202 | 0.377 | 0.389 |
| | | 7.5 | 0.108 | 0.205 | 0.244 | 0.351 | 0.381 |

Table 1-continued

| Crosslinking agent of the formula | Prepared according to Example | pH | 1/SF under normal storage after 3 hours | 1/SF under normal storage after 2 days | 1/SF under normal storage after 7 days | 1/SF under climatically controlled storage after 2 days | 1/SF under climatically controlled storage after 7 days |
|---|---|---|---|---|---|---|---|
| $R_1-HN-(CH_2)_3-N\bigcirc N-(CH_2)_3-NH-R_1$ | 6 | 6.5 | 0.082 | 0.145 | 0.207 | 0.361 | 0.358 |
| $\left[ R_1-HN-(CH_2)_3-\underset{CH_3}{\overset{CH_3}{N^\oplus}}-(CH_2)_3-NH-R_1 \right][ClO_4^\ominus]$ | 9 | 6.5 | 0.084 | 0.140 | 0.180 | 0.301 | 0.320 |
| $R_2-HN-(CH_2)_2-N\bigcirc N-R_2$ | 2 | 6.5 | 0.084 | 0.09 | 0.124 | 0.347 | 0.339 |
| $R_2-HN-(CH_2)_3-\underset{}{\overset{CH_3}{N}}-(CH_2)_3-NH-R_2$ | 1 | 6.5 | 0.074 | 0.139 | 0.167 | 0.326 | 0.343 |
| $\left[ R_2-HN-(CH_2)_3-\underset{CH_3}{\overset{CH_3}{N^\oplus}}-(CH_2)_3-NH-R_2 \right][PF_6^\ominus]$ | 7 | 6.5 | 0.087 | 0.123 | 0.139 | 0.257 | 0.256 |
| $R_2-HN-(CH_2)_3-N\bigcirc N-(CH_2)_3-NH-R_2$ | 3 | 6.5 | 0.087 | 0.154 | 0.189 | 0.381 | 0.366 |

What we claim is:

1. An acylurea compound which corresponds to the formula

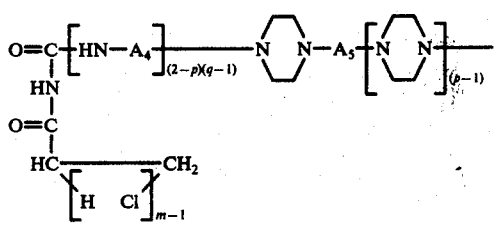

wherein $m$ is 1 or 2, $p$ and $q$ each denote one of the numbers 1 and 2 and $A_4$ and $A_5$ denote alkylene radicals with 1 to 4 carbon atoms.

2. An acylurea compound according to claim 1 which corresponds to the formula

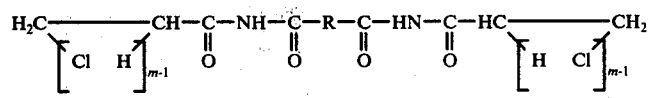

wherein R denotes one of the radicals of the formulae

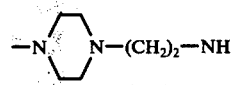

and $-HN-(CH_2)_3-N\bigcirc N-(CH_2)_3-NH-$

3. An acylurea compound according to claim 1, wherei $m$ is 1.

4. Process for crosslinking hydrophilic colloids which contain amino, imino and/or hydroxyl groups, which comprises using as a crosslinking agent a compound of the composition indicated in claim 1.

5. Process according to claim 4, which comprises crosslinking polyvinyl alcohol or gelatine.

6. Process according to claim 4, which comprises crosslinking gelatine present in a layer of a photographic material.

7. A hydrophilic colloid crosslinked by means of an acylurea compound as claimed in claim 1.

8. A layer of a photograhic material crosslinked according to claim 7.

* * * * *

UNITED STATES PATENT AND TRADEMARK OFFICE
CERTIFICATE OF CORRECTION

PATENT NO. : 4,055,431
DATED : October 25, 1977
INVENTOR(S) : Rolf Kyburz, et al.

It is certified that error appears in the above–identified patent and that said Letters Patent are hereby corrected as shown below:

In Abstract formula: "M-1" should be --m-1--.

Column 1, lines 7-8," Pat. No. 3,977,811" should read -- Pat. No. 3,977,881 --.

Column 2, lines 25-26, " > " after "HN and -N" should be -- < --

Column 7, line 40, insert --,-- after "yellowing".
Column 8, line 13, "while" should be --when--.
Column 10, lines 5&6, "dimethylammonlum" should be --dimethylammonium--.

Column 14, line 60, photograhic" should be --photographic--.

Signed and Sealed this

Sixth Day of June 1978

[SEAL]

Attest:

RUTH C. MASON
Attesting Officer

DONALD W. BANNER
Commissioner of Patents and Trademarks